(12) United States Patent
Ross et al.

(10) Patent No.: US 6,254,754 B1
(45) Date of Patent: Jul. 3, 2001

(54) CHIP FOR PERFORMING AN ELECTROPHORETIC SEPARATION OF MOLECULES AND METHOD USING SAME

(75) Inventors: Gordon Ross, Karlsruhe; Patrick Kaltenbach, Bischweier, both of (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/361,063

(22) Filed: Jul. 26, 1999

(30) Foreign Application Priority Data

Jul. 29, 1998 (EP) .................................... 98114135

(51) Int. Cl.[7] .......................... G01N 27/26; G01N 27/447
(52) U.S. Cl. .......................... 204/548; 204/450; 204/600; 204/644
(58) Field of Search .................................... 204/450, 451, 204/452, 453, 454, 455, 600, 601, 602, 603, 604, 605, 548, 644, 459

(56) References Cited

U.S. PATENT DOCUMENTS

| 5,427,663 | * | 6/1995 | Austin et al. | 204/549 |
| 5,449,446 | | 9/1995 | Verma et al. | 204/612 |
| 5,750,015 | | 5/1998 | Soane et al. | 204/454 |

FOREIGN PATENT DOCUMENTS

309303A2   8/1988   (EP) .

OTHER PUBLICATIONS

Becker et al, "Planar Quartz Chips with Submicron Channels for Two–Dimensional Capillary Electrophoresis", Journal of Micromechanics and Microengineering vol. 8, No. 1, pp. 24–28, Mar. 1998.*

European Search Report, EP 98 11 4135, Dec. 18, 1998.

Analytical Chemistry, vol. 66, No. 18, Sep. 1994, pp. 2858–2865, Daniel E. Raymond et al., "Continuous Sample Pretreatment Using a Free–Flow Electrophoresis Device Integrated onto a Silicon Chip".

Journal of Micromechanics and Microengineering, vol. 8, No. 1, Mar. 1998, pp. 24–28, H. Becker et al., "Planar Quartz Chips with Submicron Channels for Two–dimensional Capillary Electrophoresis Applications".

* cited by examiner

*Primary Examiner*—Jill Warden
*Assistant Examiner*—John S. Starsiak, Jr.

(57) ABSTRACT

A chip for performing an electrophoretic separation of micromolecular or macromolecular structures in two dimensions comprises a base substrate comprising a main surface. A channel is formed in the main surface of said base substrate in a first direction, wherein a first voltage is applicable across the channel in order to allow a separation of micromolecular structures or macromolecular structures in the first direction on the basis of a first separation mechanism. In addition, a two-dimensional separation matrix is formed in the main surface of the base substrate, wherein the separation matrix comprises a shallow recess and an array of stand-alone posts arranged in the recess. The recess extends perpendicular from the channel in a second direction, wherein a second voltage is applicable across the separation matrix in order to allow a separation of the structures on the basis of a second separation mechanism.

11 Claims, 3 Drawing Sheets

CHIP FOR PERFORMING AN ELECTROPHORETIC SEPARATION OF MOLECULES AND METHOD USING SAME

BACKGROUND OF THE INVENTION

1. Field of the Invention

The present invention relates to the electrophoretic separation of molecules, in particular proteins and, more specifically, to the electrophoretic separation in two dimensions, a first separation using an isoelectric focusing technique along a first direction and a second separation according to the molecular weight of the molecules along a second direction.

2. Description of Prior Art

The study of life sciences involves classification and characterisation of a variety of biomolecules. The study of proteins is ubiquitous in life sciences and many techniques have been used to isolate, separate and characterise proteins from a variety of sources. Established techniques for protein separation included electrophoresis and liquid chromatography. Traditionally electrophoretic techniques have been used to separate and characterise proteins. Proteins, in common with the majority of biomolecules are charged or can be made to be charged by defining the media in which they are solved. Consequently they will move, in solution, under the influence of an electric field with a velocity which is dependent on the charge to mass ratio of the protein; when the molecule has no charge it has no mobility.

Two traditional electrophoretic techniques for protein separation are isoelectric focusing (IEF) and SDS-PAGE.

IEF will separate proteins on the basis of their isoelectric point. Most proteins carry a number of charged or chargeable side chains in addition to the N- and C-terminal moieties which are also capable of carrying a charge. Depending on the pH of the buffer in which the protein is contained, these chargeable groups will carry a 0 to +1 charge if it is an amine function, and −1 to 0 charge if it is an acid group. Since the degree of ionisation will also depend on local environment, this will result in a number of different degrees of charged states over the entire protein. At a particular and idiosyncratic pH, the mixture of positive and negative charges will balance and the protein will have a net charge of 0. This property can be harnessed to separate proteins on the basis of the pH at which their net charge is zero. This pH is referred to as the isoelectric point or pI of the protein.

IEF is operated by constructing a pH gradient between two electrodes with the highest pH at the negative electrode (cathode) and lowest pH at the positive electrode (anode). A pH gradient may be created using a complex mixture of chemicals called ampholytes. These will arrange themselves between the anode and cathode such that they create a gradient of increasing pH from the anode to the cathode. When proteins are introduced into this system, their charge will depend on the pH of the environment in which they find themselves. If the environmental pH is lower than the proteins pi, then it will have a net positive charge and will migrate towards the negative electrode. In this direction, the pH increases and the protein's net charge will become zero when the local pH is the same as it's pI. Any further movement via diffusion in the direction of the negative electrode will expose the protein to a pH higher than its pI and at this point its net charge will become negative and vice versa. The protein will then migrate back towards the positive electrode until it focuses into the pH region equal to its pI. In this way, the proteins will focus in different areas depending upon their isoelectric points and this technique allows separation on the basis of pI. If a standard mixture of proteins is used with known pI's, then the sample proteins can be characterised by calculating their pI relative to the standards. Such separations are traditionally carried out in supportive media, i.e., gels or in a capillary format.

Such techniques for performing a separation on the basis of isoelectric focusing are disclosed in U.S. Pat. No. 5,320,727, for example.

A second technique for separating proteins is to separate them on the basis of their molecular weight. This can also be achieved using electrophoretic phenomena. In this case, the proteins are incubated with a chemical (sodium dodecyl sulphate (SDS)) which has a 12-carbon tail attached to a negatively charged sulphonic acid group. The C12 chain is hydrophobic and will associate with hydrophobic regions on the protein so that the negative head is projected outwards from the protein. This is usually achieved after the protein has been denatured and the resulting protein-SDS structure is linear and negatively charged. Proteins will take up SDS molecules with a relatively constant ration of 1:1,4 (protein:SDS). Therefore, these structures will have equivalent charge to mass ratios. This means that the SDS-protein structures have similar mobilities. SDS-proteins may be separated by causing them to migrate through a sieving structure usually created by making a cross-linked gel or a solution of entangled polymers. In both cases, small SDS-protein molecules will travel faster than larger SDS-protein molecules and any mixture of these will therefore separate according to molecular weight. If a standard solution of proteins of known molecular weight is used, then the molecular weight of sample proteins may be determined by comparing their migration position relative to that of the known standard. These two techniques can be combined to provide a separation of a complex mixture of proteins firstly in one dimension by IEF and secondly by SDS-protein sieving. The combination of two separation selectivities in orthogonal directions provides a powerful way of separating very complex mixtures or of characterising a protein product. This technique is becoming widely used in the field of the separation of proteins.

One combined method for high-resolution two-dimensional electrophoresis is disclosed in U.S. Pat. No. 5,407,546. This prior art method comprises the steps of carrying out at first, on a gel base, a first separation process in a first direction by isoelectric focusing and performing thereafter a second separation process in a direction vertical to the first direction by a technique different from that of the first separation. In accordance with the method taught in this document, a predetermined quantity of an IEF mixture is dispensed upon a strip-like fleece positioned on the marginal area of a dry gel layer in order to produce an IEF plateau. At the end of a predetermined period of time, the fleece is pulled-off using a pair of tweezers such that the IEF plateau remains in the dry gel layer. Thereafter, two electrophoresis processes are carried out simultaneously using a common central cathode and two anodes which are provided in two end portions of the dry gel layer.

The gels used to support the separations are generally made by the user, although these can be purchased pre-cast. These are constructed in a planar format by mixing a polymer with a certain percentage of a cross-linker. The higher percentage of cross-linker the smaller is the pore size created. Small pore sizes are of more use for small molecules and provide better differentiation or resolution between proteins of similar molecular weights. It is often useful to cast a gel where the pore size decreases linearly in one direction. This is referred to as a gradient gel and is capable of providing better resolutions of a wide range of molecular weights.

After separation in either one or two dimensions, the proteins can be reacted with a dye, such as Coummassie Blue, which will stain the protein and allow its detection. Alternatively, the gel spot containing the protein can be cut out from the gel and the protein digested with an enzyme such as trypsin to give smaller fragments. The size and number of these fragments is dependent on the amino acid sequence of the proteins and, therefore, can be defining and idiosyncratic. Another alternative is that after separation on the gel, the proteins can be transferred via electro-blotting onto a membrane. On this membrane, the protein can be subjected to a variety of tests such as immunostaining, or digested on the membrane with e.g., trypsin. The fragments resulting from digestion on the membrane can be introduced directly into a mass spectrometer which will give the molecular weights of the fragments. The number and molecular weight of the protein can be enough to identify it when compared to a protein database. Alternatively, MS/MS (MS=mass spectroscopy) can be performed in order to sequence the peptides and, therefore, provide their amino acid sequence.

The manufacturing and use of a different structure which will separate molecules under the influence of an electric field in a sieving matrix is disclosed in U.S. Pat. No. 5,427,663. According to this document, molecules which are large pieces of DNA are separated, wherein the sieving matrix is an array of physical posts which create a physical matrix which must be manoeuvred by the DNA molecules as they are driven by the electric field across the planar structure. U.S. Pat. No. 5,427,663 discloses a sorting apparatus and method for fractionating and simultaneously viewing individual microstructures and macromolecules, such as DNA molecules, proteins and polymers. In accordance with U.S. Pat. No. 5,427,663, a substrate having a shallow receptacle located on a side thereof is provided. An array of obstacles upstanding from the floor of the receptacles is provided in order to interact with the microstructures to partially hinder the migration thereof in a migration direction through the receptacle. Electrodes for generating an electric field in the fluid medium in order to induce the migration of the microstructures are provided on two sides of the receptacle. The receptacle is covered by a transparent cover, such that the height of the receptacle is commensurate with the size of the microstructures to be sorted in the sorting apparatus. Thus, when the microstructures are caused to migrate in the fluid medium through the receptacle, the microstructures do so in essentially a single layer. This is an analogous mechanism to the sieving of SDS-proteins using cross-linked gels or entangled polymers.

General techniques for the fabrication of microstructures with high aspect ratios and great structural heights by synchrotron radiation lithography, galvanoforming and plastic moulding (LIGA process) are disclosed by E. W. Becker, et al., Microelectronic Engineering 4 (1986), pages 35 to 56.

H. Becker, et al., J. Micromech. Microeng. 8 (1998), pages 24 to 28, teaches a planar quarz chip with sub-micron channels for two-dimensional capillary electrophoresis applications. In this chip, the first separation dimension consists of a single channel, whereas the second separation dimension consists of an array of 500 channels. The channels are fabricated using reactive iron etching under maximum anisotropic conditions, yielding an aspect ratio of up to 5 for the narrow channels along which the second dimension separation is performed.

SUMMARY OF THE INVENTION

It is an objective of the present invention to provide a simple chip for performing an electrophoretic separation which provides an accurate separation and which imparts the possibility of a straight-forward post separation treatment.

This objective is achieved by a chip for performing an electrophoretic separation of micromolecular or macromolecular structures in two dimensions, comprising:
a base substrate comprising a main surface;
a channel formed in said main surface of said base substrate in a first direction, a first voltage being applicable across said channel in order to allow a separation of said micromolecular or macromolecular structures on the basis of a first separation mechanism; and
a two-dimensional separation matrix formed in said main surface of said base substrate, said separation matrix comprising a shallow recess and an array of stand-alone posts arranged in said recess, said recess extending perpendicular from said channel in a second direction, wherein a second voltage is applicable across said separation matrix in order to allow a separation of said structures on the basis of a second separation mechanism.

It is a further objective of the present invention to provide a method for performing an electrophoretic separation using such a chip.

This objective is achieved by a method for performing an electrophoretic separation of micromolecular or macromolecular structures making use of a chip as described above comprising the steps of:
introducing a pH gradient into said channel;
injecting a sample volume into said channel;
applying an electrical field across said channel by turning on said first voltage and, thus, performing a separation of said structures on the basis of said first separation mechanism;
turning off said first voltage;
incubating the separated molecules with sodium dodecyl sulphate; and
applying an electrical field across said separation matrix by turning on said second voltage and, thus, performing a separation of said structures on the basis of said second separation mechanism.

In preferred embodiments of the present invention, isoelectric focusing (IEF) is used as the first separation mechanism, whereas the second separation mechanism is based on the size or the molecular weight of the structures to be separated.

The present invention provides the capability of separating molecules, in particular proteins, into orthogonal dimensions using different separation selectivities. This capability is based on a solid fabricated structure of varying dimension or geometry which mimics the sieving effect of a gel. The structure provides for the separation of proteins according to their isoelectric point (isoelectric focusing) followed by the separation according to the molecular weight (SDS-protein separation) in an orthogonal direction.

In preferred embodiments of the present invention, the stand-alone posts are formed and arranged in said recess such that distances between posts decrease from the channel-side end of the separation matrix to the end of the separation matrix opposite thereto in the second direction, wherein the decrease of the distances is preferably a linear decrease. Thus, a selective separation along the second direction can be obtained.

In addition, preferred embodiments of the inventive chip comprise means for preventing penetration of the molecules in the second direction when the first voltage is applied across the channel by restricting an electrical field caused by the first voltage to the channel. Such a preventing means can be formed by multiple barriers arranged orthogonal to the channel at the channel-side end in the recess. In an alternative embodiment, the preventing means comprises means for applying a third voltage to the chip such that field components of the electric field caused by the first voltage which are orthogonal to the channel are substantially compensated. Thus, it can be ensured that during the separation in the first direction, the molecules do not migrate into the separation matrix. Thus, the molecules will have identical start positions along the first direction relative to the direction of the second dimension when the separation in the second direction is started. Thus, more accurate separation results can be achieved using such embodiments of the present invention.

In further embodiments of the present invention, which allow the preparation for a post-separation detection analysis, the inventive chip further comprises a cover substrate, a main surface of the cover substrate being connectable to the main surface of the base substrate such that a membrane is interposed between the main surfaces of the base substrate and the cover substrate, wherein the main surface of the second substrate is provided with a chamber facing the separation matrix when the second substrate is connected to the base substrate, wherein reagents for a post-separation detection analysis being loadable into said chamber.

Inlet and outlet channels to the second chamber allow the introduction of any reagents onto the membrane allowing enzymatic digestion, immunoreaction or staining or labelling, for example, of the separated proteins. Electrical contacts may be provided for performing an electro-blotting of the separated molecules, in particular, proteins, onto the membrane located between the base substrate and the cover substrate. The separated molecules may be visualised through the upper surface of the second chamber or, alternatively, the membrane onto which the separated molecules are electro-blotted can be removed and presented directly into a mass spectrometer or can be excised for further analysis.

Thus, the present invention provides a chip for an electrophoretic separation which can be performed in an automated manner wherein the handling of the sample can be minimised. In addition, the inventive chip permits a selective separation by providing the capability of separating molecules, in particular, proteins, into orthogonal dimensions using different separation selectivities. Furthermore, the usage of a solid fabricated structure as the sieving matrix provides reproducible results, since the solid fabricated structure can be manufactured with an accurate reproducibility.

The material used for the inventive chip is not a critical feature. However, if high volume production of chips is necessary, the material will, preferably, be a polymeric material, such as PMMA (polymethylmethacrylate), polycarbonate, polyethyleneterephtalate, polystirene or PDMS (polydimethylsiloxane). In addition, any suited manufacturing technique can be used. The manufacturing technique may range from micro-injection moulding to micro-transfer moulding. For example, the techniques disclosed in the article of E.W. Becker mentioned above can be used to manufacture the inventive chip. In either case, the polymeric material should be substantially non-porous and have no or negligible surface charge to suppress electroendosmosis. If necessary, an additional polymeric coating can be used.

BRIEF DESCRIPTION OF THE DRAWINGS

Preferred embodiments of the present invention will be described hereinafter referring to the appended drawings, in which.

DESCRIPTION OF PREFERRED EMBODIMENTS OF THE INVENTION

Figure 1:
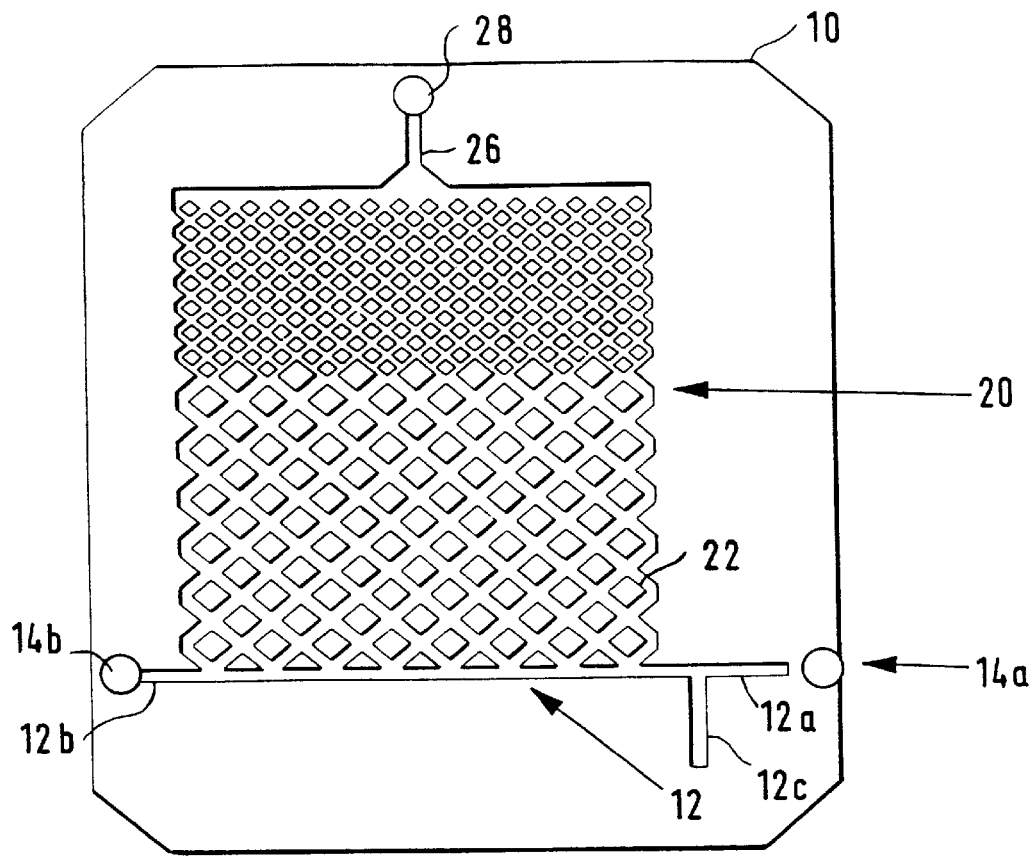
FIG. 1 shows a schematic top view of an embodiment of the inventive chip.
Figure 2:
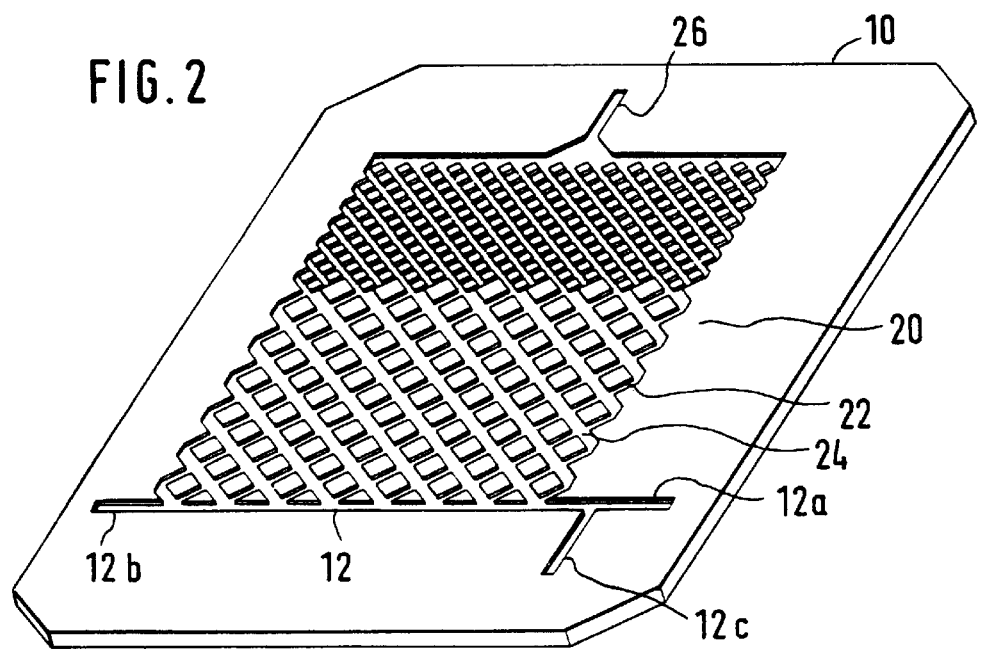
FIG. 2 is a perspective view of the chip shown in FIG. 1.

Referring now to FIGS. 1 and 2, a first embodiment of the present invention will be explained in detail. In the following description, the present invention is mainly described referring to the electrophoretic separation of proteins. However, it is clear for skilled persons that the present invention is applicable to the electrophoretic separation of different micromolecular structures and macromolecular structures as well.

The inventive chip for performing an electrophoretic separation of proteins comprises a channel 12 formed in one main surface of a base substrate 10 of the chip and extending in one direction thereof. The channel 12 comprises an inlet 12a and an outlet 12b. A buffer can enter the channel 12 via the inlet 12a and can leave the channel 12 via the outlet 12b. The inlet 12a is in fluidic communication with a buffer reservoir, whereas the outlet 12b is in fluidic communication with a waste buffer reservoir. An injection channel 12c is provided in fluidic communication with the inlet 12a for an injection of a sample. Furthermore, electrodes, which are schematically shown in FIG. 1 with reference numbers 14a and 14b, are provided for applying a voltage across the channel 12.

The channel is used to perform the IEF separation in the first direction. The pH gradient necessary for performing a separation by isoelectric focusing can be created by introducing a liquid carrier containing a complex mixture of chemicals called ampholytes. Alternatively, a membrane (not shown) can be used in order to provide the pH gradient. Making use of a membrane is preferred, since a more reproducible pH gradient can be obtained.

For the separation in the second direction, a separation matrix 20 is provided in the same main surface of the substrate 10 as the channel 12 is. The separation matrix consists of a fabricated array of posts 22. As can be seen from FIG. 2, the posts 22 are arranged in a recess 24, which is formed in the main surface of the substrate 10. At one side thereof, the recess 24 is connected to the channel 12. At the end side of the recess 24 opposite to the channel-side thereof, an outlet channel 26 is provided.

The posts 22 can either be uniform to provide a similar analogous pore size across the separation matrix or of varying geometries or densities so that the "pore size" varies across the separation matrix. In the embodiment shown in FIGS. 1 and 2, the posts arranged toward the channel-side of the separation matrix define a wider "pore-size" as compared with the posts arranged toward the outlet-side of the separation matrix. In preferred embodiments, the posts provide a linear gradient of decreasing pore sizes from the channel-side of the separation matrix to the outlet-side thereof. Preferably, the depth of the recess 24, i.e., the height of the posts 22 is matched to the size of the proteins, molecules or microstructures which are to be separated such that the substances to be separated will migrate through the separation matrix. When the substances migrate through the separation matrix, the posts 22 will hinder the migration depending on the size of the respective molecules such that a separation in the direction from the channel 12 to the outlet 26 can be obtained.

In order to provide the migration of the proteins through the separation matrix, a further electrode, schematically depicted in FIG. 1 at 28, is provided for applying a voltage across the separation matrix and, thus, for generating an electric field in order to induce the migration of the molecules.

While three electrodes 14a, 14b and 28 are schematically shown in FIG. 1, it is clear that the inventive chip can incorporate various electrical connections in an appropriate arrangement, so that an electric field can be applied across any pair of opposing or adjacent faces.

For performing a separation making use of the chip described above, a buffer is introduced into the channel 12 via inlet 12a, wherein a pH gradient is caused either by a liquid carrier or by a membrane (not shown). Thereafter, a sample volume is injected into the channel 12 via the injection channel 12c. Thereafter, an electrical field is applied across the channel 12 via electrodes 14a and 14b by turning on a first voltage. Under the influence of this electrical field, an isoelectric focusing separation of the proteins in the sample is performed. After the isoelectric focusing is complete, the first voltage is turned off and the separated molecules are incubated with SDS (sodium dodecyl sulphate) on the planar structure at room temperature. After creating the SDS molecule complexes, the direction of polarity is switched by applying a second voltage between the electrodes 28 and 14a, 14b, such that the SDS molecule complexes, for example, the negatively charged SDS protein complexes, will migrate through the fabricated array and separate according to their molecular weight. Thus, the separation is completed.

It is obvious for skilled people that, while preferred embodiments of the present invention relate to the separation of proteins, the present invention can be applied for the separation of different micromolecular structures or macromolecular structures. In either case, the dimensions of the separation matrix, i.e., the size of the posts and the distances therebetween, should be adapted to the respective structures to be separated. The form and the pattern of the posts are not restricted to the particular form and the particular pattern shown in the Figures. Rather, the posts can accept any desired form and can be arranged in any desired pattern such that the desired electrophoretic separation can be achieved.

Figure 3:
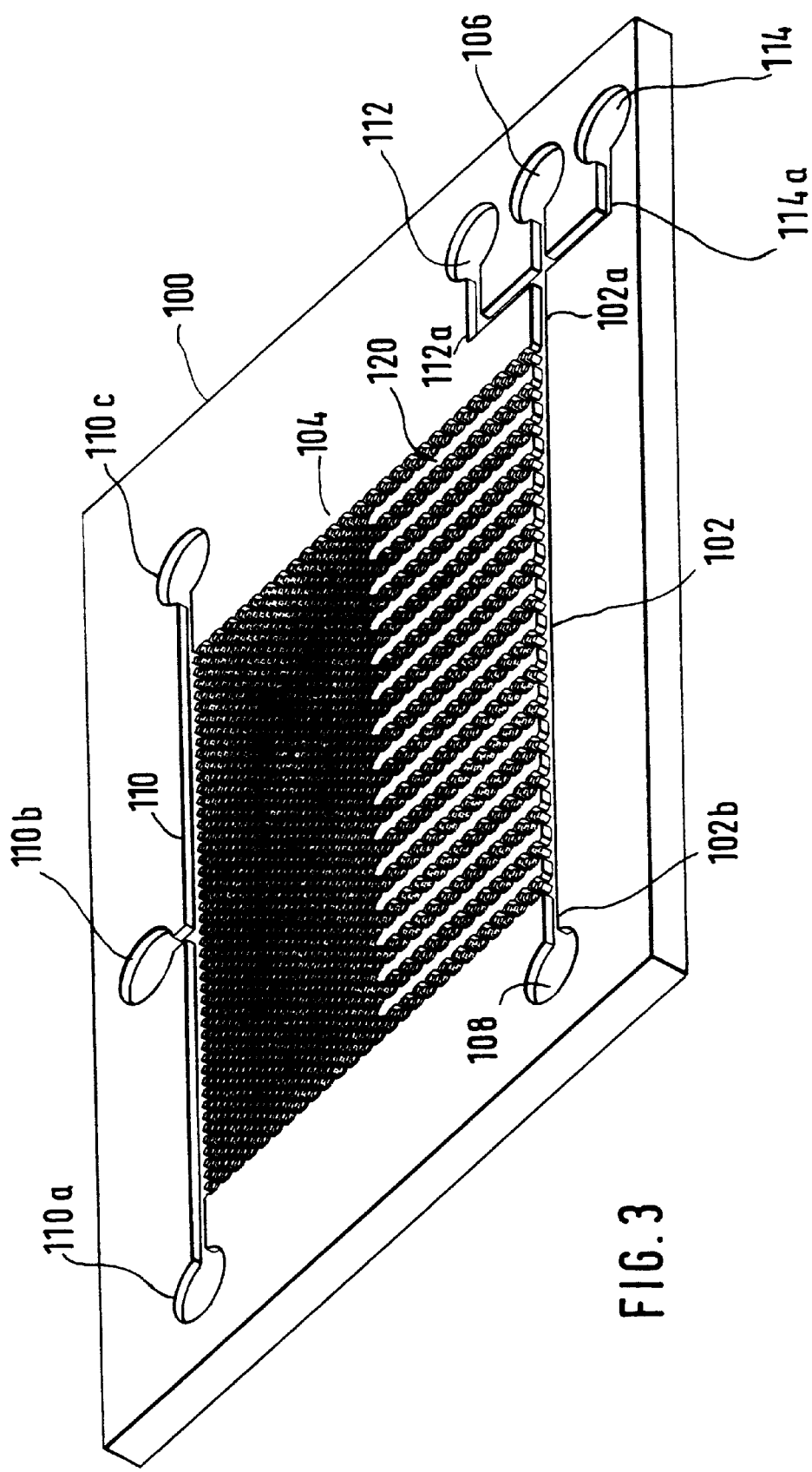
FIG. 3 is a schematic perspective view of a further embodiment of the inventive chip.
Figure 4:
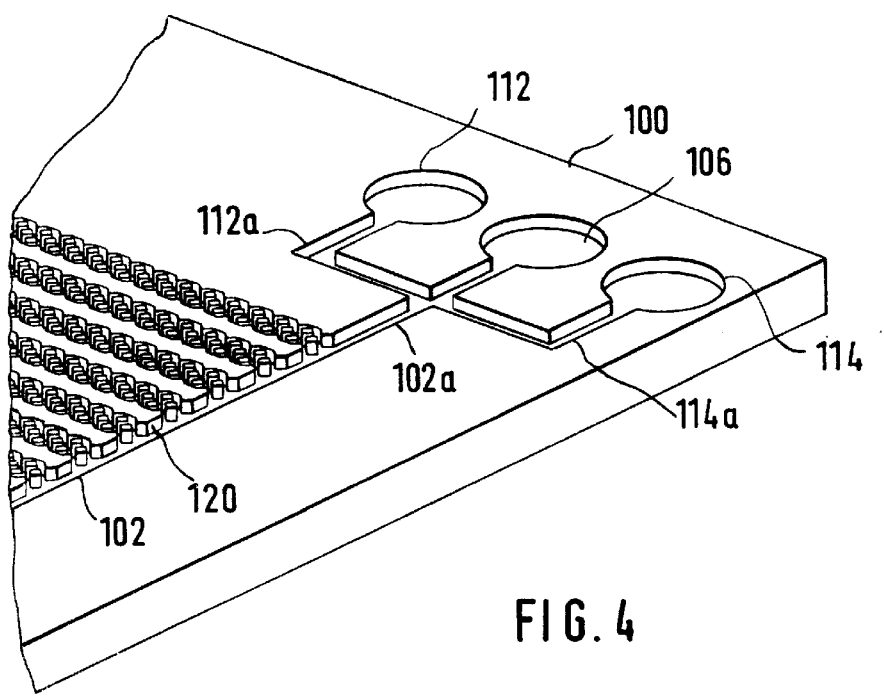
FIG. 4 is an enlarged view of the lower right corner of the chip shown in FIG. 3.

A further embodiment of the present is shown in FIGS. 3 and 4. A substrate 100 comprises an IEF channel 102 and a separation matrix 104 in one main surface thereof. Again, the separation matrix is formed by a multitude of posts arranged in a recess formed in the main surface of the substrate. The channel 102 comprises an inlet 102a and an outlet 102b. The inlet is in fluidic communication with a buffer reservoir 106, whereas the outlet 102b is in fluidic communication with a waste buffer reservoir 108. Furthermore, an outlet channel 110 is provided at the outletside of the separation matrix 104. The outlet channel 110 can be in fluidic communication with cavities 110a, 110b and 110c for receiving waste buffer. As can be best seen in FIG. 4, which is an enlarged representation of the lower right section of the chip shown in FIG. 3, a sample cavity 112 and a waste cavity 114 are provided in the main surface of the substrate 100. The sample cavity 112 is connected to the inlet 102a by a sample channel 112a. The waste cavity 114 is connected to the inlet 102a by a waste channel 114a. As can be seen from FIG. 4, the channel inlet 102a, the sample channel 112a and the waste channel 114a are arranged to form a cross.

A sample is injected by moving the sample from the sample cavity 112 to the waste cavity 114 by application of an electric field between the two cavities. The cross between the channel inlet 102a, the sample channel 112a and the waste channel 114a determines the injection volume for the following IEF separation. As has been described referring to FIGS. 1 and 2, the IEF separation is performed by applying an electrical field between the buffer cavities 106 and 108.

In order to avoid penetration of the sample into the array of posts 104 during the IEF separation in the channel 102, it is preferred to keep the electrical field in the separation channel 102. As can be seen from FIGS. 3 and 4, this is accomplished in accordance with a preferred embodiment of the present invention by providing multiple barriers 120 which are orthogonal to the channel. The barriers 120 are effective to restrict the electrical field caused by a voltage applied across the channel 102 to the channel 102. Without these barriers 120, the electrical field would partially spread into the array structure and the sample constituents would follow the field lines. This is suppressed by the barriers 120.

In an alternative embodiment, a spreading of the sample constituents into the array structure during the IEF separation is prevented by providing means for applying a third voltage to the chip such that field components of the electric field caused by the voltage across the channel 102 which are orthogonal to the channel 102 are substantially compensated. This might be achieved by applying a corresponding appropriate electrical field between the cavities 110a and 110c, such that the field components which are orthogonal to the channel 102 are suppressed.

After the IEF separation is completed, the voltage across the channel 102 is turned off, the separated constituents are incubated with SDS and a voltage is applied across the array of the posts to perform the second dimension separation in a direction orthogonal to the channel 102. The barriers are now in line with the electrical field and will not disturb the separation in the second direction.

Figure 5:
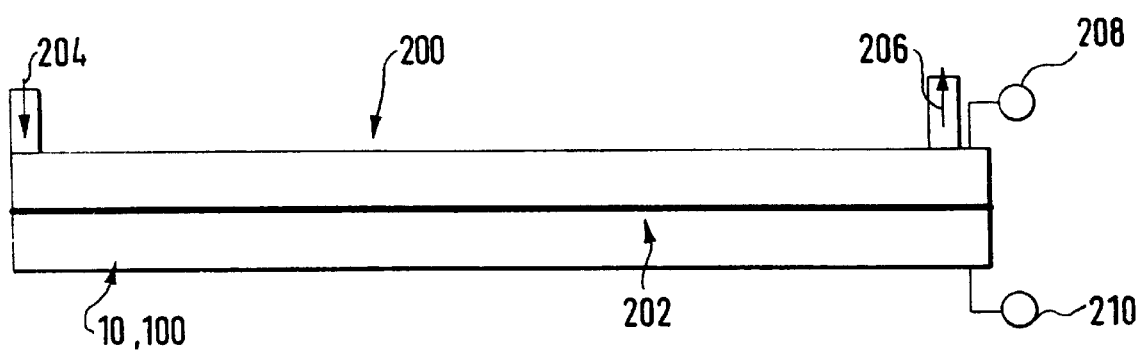
FIG. 5 is a schematic side view of an embodiment of the present invention comprising a main substrate and a cover substrate.

Referring to FIG. 5, an embodiment of the inventive chip comprising a post separation treatment unit is described. The post separation treatment unit comprises a cover substrate 200 which is adapted to be connected to the base substrate 10 or 100. One surface of the cover substrate 200, in which a chamber is provided, can be connected to the main surface of the base substrate, in which the separation structures are defined, such that the chamber of the cover substrate faces the separation matrix. Furthermore, a membrane 202 made, for example, of polyvinylidenefluoride can be arranged sandwiched between the cover substrate 200 and the base substrate and, therefore, between the separation matrix and the chamber defined in the cover substrate 200.

In addition, the cover substrate 200 comprises a reagent inlet 204 and a reagent outlet 206. Via the reagent inlet 204 reagents may be introduced into the chamber defined in the cover substrate after the separation in the second direction is complete. In addition, electrical contacts 208 and 210 can be provided in order to allow an electro-blotting of the separated proteins onto the membrane 202. Moreover, the inlet channel 204 and the outlet channel 206 which are in fluidic communication with the chamber in the cover substrate 200, permit the introduction of any reagents onto the membrane allowing further chemical reactions, e.g., enzymatic digestion, immunoreaction or staining or labelling.

It is to be noted that the cover substrate 200 is removable from the base substrate and can be separated therefrom. Thus, the membrane can be removed and presented directly into a mass spectrometer or excised for further analysis. It is to be noted that the entire structure is capable of being thermostated at varying temperatures and the separated proteins may be visualised through the upper surface of the cover substrate 200, i.e., the upper surface of the chamber therein. In this way, the handling of the sample is minimised.

It is to be noted that the term "chip" used herein refers to a shape that is generally rigid, thin and small and handable by human fingers. The substrate or substrates forming the chip are rigid sheets of preferably polymeric materials, such as PMMA, polycarbonate, polyethyleneterephtalate, polystirene or PDMS. In addition, the substrates can be formed of silicon and silicon dioxide using lithography and refractive ion etching as manufacturing techniques. The structures in the substrates may be microstructured by any lithographic techniques and microstructuring processes, for example, laser application or etching. Furthermore, the substrates may be micro-injection moulded (LIGA processes).

Finally, it is to be noted that a plurality of detection methods are applicable, wherein the detection can be based on laser-induced fluorescence or on densiometers, preferably with a scanning detector or a CCD.

Finally, it is to be noted that the length of the barrier 120 of the embodiment of the invention shown in FIGS. 3 and 4 is chosen such that a sufficient electrical resistence is provided to suppress a migration of the sample constituents in a direction orthogonal to the IEF separation channel during the IEF separation. In this regard, the length of the barriers 120 may be in the range of one third to two thirds of the length of the separation matrix.

What is claimed is:

1. A chip for performing an electrophoretic separation of molecular structures in two dimensions, comprising:
   a base substrate comprising a main surface;
   a channel formed in said main surface of said base substrate in a first direction, a first voltage being applicable across said channel in order to allow a first separation of said molecular structures in said first direction on the basis of a first separation mechanism;
   a two-dimensional separation matrix formed in said main surface of said base substrate, said separation matrix comprising a shallow recess and an array of stand-alone posts arranged in said recess, said recess extending perpendicular from said channel in a second direction, wherein a second voltage is applicable across said separation matrix in order to allow a second separation of said molecular structures on the basis of the basis of a second separation mechanism; and
   means for preventing penetration of the molecular structures in said second direction when said first voltage is applied across said channel by restricting an electrical field caused by said first voltage to said channel.

2. The chip of claim 1, wherein the posts are formed and arranged in said recess such that distances between posts decrease from the channel-side end of the separation matrix to the end of the separation matrix opposite thereto in the second direction.

3. The chip of claim 2, wherein the posts are formed and arranged in said recess such that the decrease of the distances is a linear decrease.

4. The chip of claim 1, wherein said preventing means is formed by multiple barriers arranged orthogonal to said channel at the channel-side end in said recess.

5. The chip of claim 1, wherein said preventing means comprises means for applying a third voltage to said chip such that field components of the electrical field caused by said first voltage which are orthogonal to said channel are substantially compensated.

6. The chip of claim 1, wherein the channel comprises an inlet connected to a buffer reservoir and further connected to a sample cavity and a waste sample cavity such that a sample can be injected into said channel by applying an electrical field between said sample cavity and said waste sample cavity.

7. The chip of claim 1, further comprising a cover substrate, a main surface of said cover substrate being connectable to the main surface of said base substrate such that a membrane is interposed between said main surfaces of the base substrate and the cover substrate, wherein said main surface of said cover substrate is provided with a chamber facing said separation matrix when said cover substrate is connected to said base substrate, reagents for a post separation detection analysis being loadable into said chamber.

8. The chip of claim 7, further comprising means for applying an electrical field between said base substrate and said cover substrate for allowing electro-blotting of separated molecules onto said membrane.

9. The chip of claim 1, wherein said first separation mechanism is isoelectric focusing.

10. The chip of claim 1, wherein said second separation mechanism is according to the molecular weight of the molecular structures.

11. A method for performing an electrophoretic separation of molecules making use of a chip according to claim 1, comprising the steps of:
   introducing a pH gradient into said channel;
   injecting a sample volume into said channel;
   applying an electrical field across said channel by turning on said first voltage and, thus, performing a separation of said molecular structures on the basis of said first separation mechanism;
   turning-off said first voltage;
   incubating the separated molecules with sodium dodecyl sulphate;
   applying an electrical field across said separation matrix by turning on said second voltage and, thus, performing a separation of said molecular structures on the basis of said second separation mechanism.

* * * * *